United States Patent
Geremia et al.

(10) Patent No.: US 6,342,597 B1
(45) Date of Patent: *Jan. 29, 2002

(54) 1,4,7,10-TETRAAZACYCLODODECANE-1,4-DIACETIC ACID DERIVATIVES AS CHELATING AGENTS

(75) Inventors: Renato Geremia; Marcella Murru; Giorgio Ripa; Vittorlo Valle, all of Milan (IT)

(73) Assignee: Dibra S.p.A., Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 09/582,662

(22) PCT Filed: Dec. 18, 1998

(86) PCT No.: PCT/EP98/08330

§ 371 Date: Aug. 25, 2000

§ 102(e) Date: Aug. 25, 2000

(87) PCT Pub. No.: WO99/35133

PCT Pub. Date: Jul. 15, 1999

(30) Foreign Application Priority Data

Dec. 30, 1997 (IT) .......................... MI97A2896

(51) Int. Cl.$^7$ ................... C07D 257/02; C07D 257/10; C07D 241/36
(52) U.S. Cl. ............... 540/465; 540/472; 540/474
(58) Field of Search .............. 540/465, 472, 540/474

(56) References Cited

U.S. PATENT DOCUMENTS 5,132,409 A * 7/1992 Felder et al. ............ 534/10
5,410,043 A * 4/1995 Platzek et al. .......... 540/465

FOREIGN PATENT DOCUMENTS

| EP | 0 299 795 A | 1/1989 |
|---|---|---|
| EP | 0 448 191 A | 9/1991 |
| EP | 0 481 420 A | 4/1992 |
| EP | 0 545 511 A | 6/1993 |
| EP | 0 872 479 A | 10/1998 |
| FR | 2 736 051 A | 1/1989 |
| WO | 89 05802 A | 6/1989 |
| WO | 95 05118 A | 2/1995 |
| WO | WO-95/05118 A1 * | 2/1995 |
| WO | 95 09161 A | 4/1995 |
| WO | WO-97/00087 A1 * | 1/1997 |
| WO | WO-97/36619 A2 * | 10/1997 |
| WO | 99 05128 A | 2/1999 |
| WO | 99 05145 A | 2/1999 |

OTHER PUBLICATIONS

Aime et al, Inorg. Chem. 31 (1992) 1100–1103.*
Meunier et al, Can. J. Chem. 73 (1995) 685–695.*

* cited by examiner

Primary Examiner—John M. Ford
Assistant Examiner—A A Kahsay Habte
(74) Attorney, Agent, or Firm—Nixon & Vanderhye

(57) ABSTRACT

Compounds of formula (I)

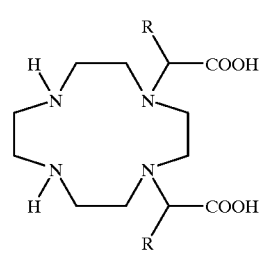

(I)

in which R is in which R is hydrogen, a straight or branched or cyclic $C_1$–$C_6$ alkyl group, unsubstituted or substituted by 1 to 10 oxygen atoms, or a $C_1$–$C_{20}$ alkyl group, optionally interrupted by a phenylene, in turn substituted by a straight or branched $C_1$–$C_6$ alkyl group, unsubstituted or substituted by 1 to 3 $C_1$–$C_7$ alkyl groups; the phenylene group being unsubstituted or substituted by alkoxy, carboxy, sulfamoyl, hydroxyalkyl, amino groups; as well as its complexes with a bi- or trivalent metal ion having an atomic number from 20 to 31, 39, 42, 43, 44, 49, or from 57 to 83, as well as its salts with anions of physiologically acceptable organic acids chelated complexes of these compounds are used as contrast agents for nuclear magnetic resonance imaging.

24 Claims, No Drawings

1,4,7,10-TETRAAZACYCLODODECANE-1,4-DIACETIC ACID DERIVATIVES AS CHELATING AGENTS

The present invention relates to the novel 1,4,7,10-tetraazacyclododecane-1,4-diacetic acid derivatives of formula (I), their complexes with paramagnetic metal ions and physiologically compatible salts thereof, as well as to the preparation thereof and the use thereof for the preparation of chelating agents.

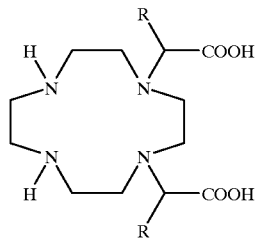

(I)

In particular the present invention relates to the derivatives of the novel compound, 1,4,7,10-tetraazacyclododecane-1,4-diacetic acid of formula (X), its chelated complex salts with pararnagnetic metal ions and the physiologically compatible salts thereof, as well as to the preparation thereof and the use thereof for the preparation of chelating agents.

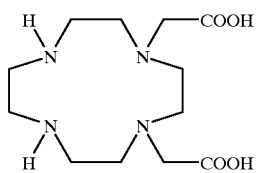

(X)

The compounds of general formula (I), and in particular the compound of formula (X), are novel chelating agents for bi- trivalent metal ions and are also important intermediates for the synthesis of 1,4,7,10-tetraazacyclododecane derivatives chelating agents, symmetrically functionalized at the 1- and 4-positions.

The compounds of general formula (I) are therefore the starting material for the synthesis of multidentate derivatives which are capable of complexing different metals, some of which have applications in the biomedical field, such as gadolinium complexes of said derivatives, which are used in diagnostic as contrast agents for the magnetic resonance technique (Magnetic Resonance Imaging, MRI).

In particular, the medical diagnosis by means of "Magnetic Resonance Imaging" (M.R.I.), which is known to be a powerful diagnostic means in the clinical practice (Stark, D. D., Bradley, W. G., Jr., Eds. "Magnetic Resonance Imaging" The C. V. Mosby Company, St. Louis, Mo. (USA), 1988), mainly makes use of paramagnetic pharmaceutical compositions, preferably containing chelated complex salts of bi- and trivalent paramagnetic metal ions with aminopolycarboxylic acids and/or derivatives or analogues thereof.

Presently some of them are used in clinic as M.R.I. contrast agents (Gd-DTPA, N-methylglucamine salt of the gadolinium complex with diethylenetriaminopentaacetic acid, MAGNEVIST®, Schering; Gd-DOTA, N-methylglucamine salt of the gadolinium complex with 1,4,7,10-tetraazacyclododecane-1,4,7,10-tetraacetic acid, DOTAREM®, Guerbet).

A list of significant patent literature for illustrating the prior art in this diagnostic field, although only exemplary and incomplete, is the following: EP 71564 (Schering), U.S. Pat. No. 4,639,365 (Sherry), U.S. Pat. No. 4,615,879 (Runge), DE-A-3401052 (Schering), EP 130934 (Schering), EP 65728 (Nycomed), EP 230893 (Bracco), U.S. Pat. No. 4,826,673 (Mallinckrodt), U.S. Pat. No. 4,639,365 (Sherry), EP 299795 (Nycomed), EP 258616 (Salutar), WO 8905802 (Bracco).

Object of the present invention are the compounds of general formula (I):

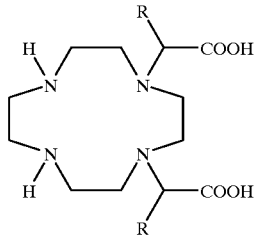

(I)

in which
R is a hydrogen atom, a straight or branched or cyclic $C_1$–$C_6$ alkyl group, unsubstituted or substituted by 1 to 10 oxygen atoms, or a $C_1$–$C_{20}$ alkyl group, optionally interrupted by a phenylene, in its turn substituted by a straight or branched $C_1$–$C_6$ alkyl group, unsubstituted or substituted by 1 to 3 $C_1$–$C_7$ groups; the aromatic group being unsubstituted or substituted by alkoxy, carboxy, sulfamoyl, hydroxyalkyl, amino groups; as well as their complexes with bi-trivalent metal ions having atomic number variable from 20 to 31, 39, 42, 43, 44, 49, or from 57 to 83, as well as their salts with anions of physiologically acceptable organic acids, selected, for example, from acetate, succinate, citrate, fumarate, maleate, oxalate, or with anions of inorganic acids such as halo acids ions, namely chlorides, bromides, iodides. Metal ions suitable for preparing complex salts with the novel chelating agents of general formula (I) are mainly bivalent or trivalent ions of the elements having atomic number variable from 20 to 31, 39, 42, 43, 44, 49, or from 57 to 83; particularly preferred being $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$ or also radioisotopes as $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$, $^{212}Bi$.

Preferably R can be selected from the group consisting of: H or a straight or branched alkyl group, such as a methyl, ethyl, propyl, isopropyl, butyl, isobutyl group, in its turn substituted by hydroxy groups or interrupted by oxygen atoms, as defined above.

When an aromatic group is present in R, particularly preferred are the phenyl and benzyl groups.

Particularly preferred are the compounds of formula (I) selected from the group consisting of: α,α'-dimethyl-1,4,7,10-tetraazacyclododecane-1,4-diacetic acid; α,α'-diethyl-1,4,7,10-tetraazacyclododecane-1,4-diacetic acid; and α,α'-dibenzyl-1,4,7,10-tetraazacyclododecane-1,4-diacetic acid.

Preferred anions of inorganic acids suitable for salifying the chelated complexes of the invention comprise, in particular, halo acids ions such as chlorides, bromides, iodides or other ions, such as sulfate.

Preferred anions of organic acids suitable for the above aim comprise those of the acids conventionally used in pharmaceutical technique for the salification of basic substances, such as acetate, succinate, citrate, fumarate, maleate.

Preferred amino acids anions comprise, for example, those of taurine, glycine, lysine, arginine or ornithine, or of aspartic and glutamic acids.

The formation of the complex metal salt is carried out conventionally, preferably in water or in a suitable wateralcohol mixture, by reacting compounds (I) with a metal salt (oxide or halide), whereas the temperature can range from 25° C. to 100° C., preferably from 40° C. to 80° C.

The choice of the metal ion and of any neutralizing ion is closely related to the intended use of the complex to be prepared.

The preparation of the novel compound, manganese complex of 1,4,7,10-tetraazacyclododecane-1,4-diacetic acid, which is in the neutral form and therefore does not require the formation of a physiologically compatible salt, is described in the Experimental section.

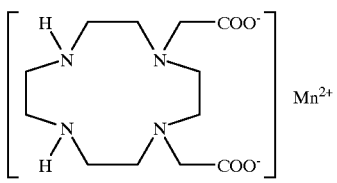

The novel compounds of the present invention have a good tolerability; moreover, their water solubility and the low osmolality of their solutions are a further advantageous characteristic which makes them particularly suitable for use in nuclear magnetic resonance.

Both soluble and less soluble compounds are useful for the oral and enteral administrations and, therefore, for the imaging of the GI tract.

As far as the parenteral administration is concerned, the compounds are preferably formulated as a sterile aqueous solution or suspension, whose pH can range for instance from 6.0 to 8.5.

These aqueous solutions or suspensions can be administered in concentrations ranging from 0.002 to 1.0 mol.

These formulations can be lyophilized and supplied as they are for reconstitution before use. For the GI use or for the injection in the body cavities, such agents can be formulated as a solution or suspension containing suitable additives, for example thickeners.

In the oral administration they can be formulated according to preparation methods commonly used in the pharmaceutical practice possibly as coated formulations in order to get additional protection from the stomach acid pH, by preventing the release of the chelated metal ion occurring in particular at pH typical of gastric juices.

Other excipients, for instance sweeteners and/or flavouring agents, can also be added according to known techniques of pharmaceutical formulation.

The chelated complex salts of this invention can also be used as radiopharmaceuticals in nuclear medicine, both in the diagnostic and therapeutic sector.

In this case, however, the metal ion which is chelated is a radioisotope, for instance $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$ and $^{212}Bi$.

The compounds of the invention can optionally be chemically conjugated with suitable macromolecules or included in suitable carriers.

It is also an object of the invention the process for the preparation of the compounds of general formula (I) starting from triethylenetetramine of formula (II) comprising the following steps represented in Scheme 1:

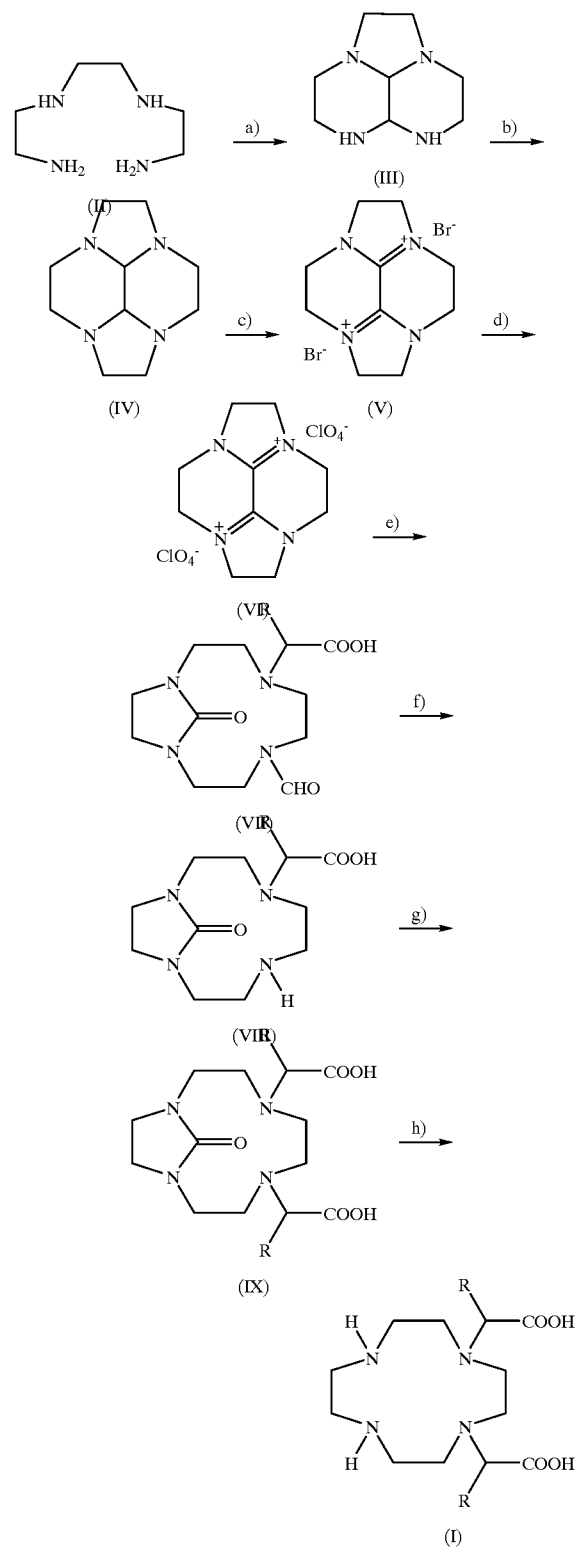

a) condensation of triethylenetetramine of formula (II) with a glyoxal derivative (glyoxal hydrate, or Bertagnini's salt), in water or in water-soluble solvents or in mixtures thereof, at a temperature of 0–50° C., in the presence of a stoichiometric amount or a slight excess of calcium hydroxide to give octahydro-3H,6H-2a,5,6,8a-tetraazacenaphthylene of formula (III);

b) condensation of the compound from step a) with an alkylating agent X—CH$_2$—CH$_2$—X, in which X is Cl or Br in amounts from 1 to 5 mols per mol of compound (III), in a dipolar aprotic solvent and in the presence of a base selected from alkali or alkaline-earth metal carbonates, in amounts from 5 to 10 mols per mol of compound (III), and with the addition of NaY, wherein Y is I or Br, as catalyst in amounts from 0.1 to 2 mols per mol of compound (III), wherein X and Y are not at the same time Br, at a temperature from 25 to 150° C., to give decahydro-2a,4a,6a,8a-tetraazacyclopent[fg]acenaphthylene of formula (IV);

c) oxidation of compound (IV) with bromine at pH 4–5 to give 2,3,4,6,7,8-hexahydro-1H,5H-4a,6a-diaza-2a,8a-azoniacyclopent[fg]acenaphthylene dibromide of formula (V);

d) formation of 2,3,4,6,7,8-hexahydro-1H,5H-4a,6a-diaza-2a,8a-azoniacyclopent[fg]-acenaphthylene diperchlorate of formula (VI), poorly water-soluble, by addition of perchlorate ions to the solution of compound (V);

e) alkylation of compound of formula (VI) with an alkylating agent of formula R—CH(X)COOH, in which X is a halogen, and R is defined as above, in basic conditions, to give the novel compounds of formula (VII);

f) hydrolysis of the formyl group of compounds (VII) in basic conditions to give the novel compounds of formula (VIII);

g) alkylation of compound (VIII) with the alkylating agent of formula R—CH(X)—COOH, in which X and R have the meanings defined above, in basic conditions, to give the novel compounds of formula (IX);

h) final hydrolysis of compounds (IX), in basic conditions, to give the compounds of formula (I).

The process of the present invention requires no isolation of the intermediate compounds, although this has been carried out to correctly identify their structures by means of various analytic techniques.

The process of the invention is particularly useful from the industrial point of view since it allows to prepare compounds (I) from inexpensive precursors such as triethylenetetramine, instead of expensive macrocyclic derivatives.

Steps a) and b) are object of Italian Patent application MI 97A000783, in the Applicant's name, and provide compound (IV) in good yields.

In particular, in step b), the alkylating agent is generally added in amounts from 1 to 5 mols per mol of compound (III).

The reaction takes place in dipolar aprotic solvents, preferably selected from the group consisting of: DMAC (dimethylacetamide), DMF (dimethylformamide), DMSO (dimethylsulfoxide) and N-methyl-pyrrolidone; and in the presence of an inorganic base, preferably an alkali metal carbonate.

The temperature, depending on the solvent and on the alkylating agent, can range from 25 to 150° C., preferably from 30 to 80° C. The reaction time is 1–48 h.

More specifically, when using 1,2-dichloroethane and NaBr, temperature ranges from 50 to 80° C. and the reaction time ranges from 2 to 5 h.

When using 1,2-dichloroethane and NaI, temperature ranges from 30 to 50° C. and the reaction time ranges from 5 to 15 h.

Step c) is the oxidation with bromine in amounts of 2–2.5 mols per mol of compound (IV) in aqueous solution at pH of 4–5, obtained by addition of an acid and kept during the reaction by addition of a base, preferably NaOH or KOH.

The reaction temperature ranges from 17 to 30° C. and the reaction time is usually 16 hours.

At the end of the reaction, and this is step d) of the present invention, sodium perchlorate or perchloric acid are added in amounts ranging from 2.5 to 3 mols per mol of compound (IV), thereby precipitating compound (VI) in good yields.

The alkylation conditions in step e) are usual in literature.

Particularly preferred are the alkylating agents of formula R—CH(X)—COOH in which X is bromine or chlorine and most preferred are the alkylating agents of formula XCH$_2$COOH, in which R is the hydrogen atom and X is bromine or chlorine.

The alkylation reaction is usually carried out in the following conditions: the reaction temperature can range from 30 to 70° C.; the reaction time usually ranges from 10 to 25 hours; basic pH from 10 to 12 is obtained by addition of a base, preferably sodium or potassium hydroxide; the amount of alkylating agent is stoichiometric or in a slight excess (1÷2 mols).

Step f) is the hydrolysis of compounds (VII) in aqueous solution at pH made basic by addition of a base, preferably NaOH or KOH, at temperatures ranging from 50 to 100° C.

Step g) is effected as already described for step e).

Step h) is the hydrolysis of compounds (IX) in aqueous solution at pH made basic by addition of 3–7 mols of a base, preferably NaOH or KOH, at temperatures ranging from 150–220° C.

Particularly preferred is the process of the invention for the preparation of compound (X), according to the following Scheme 2:

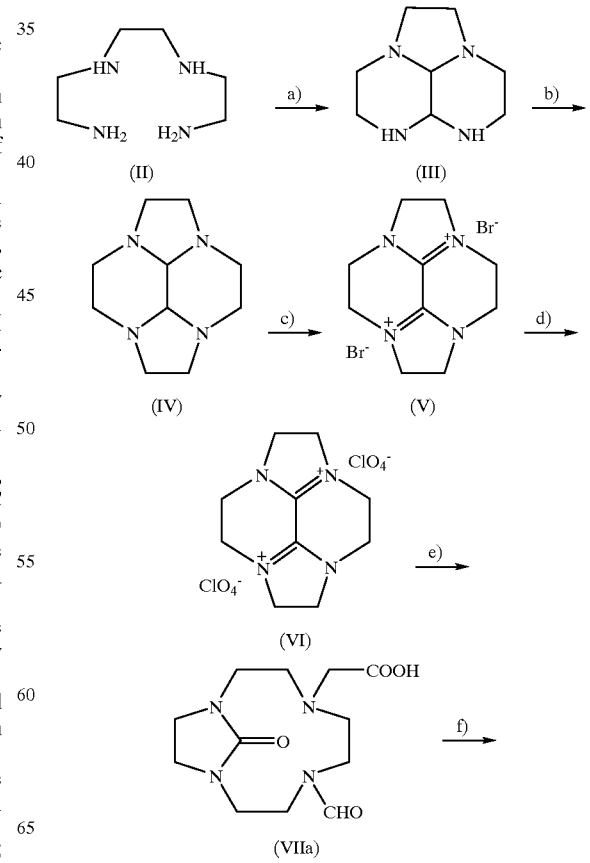

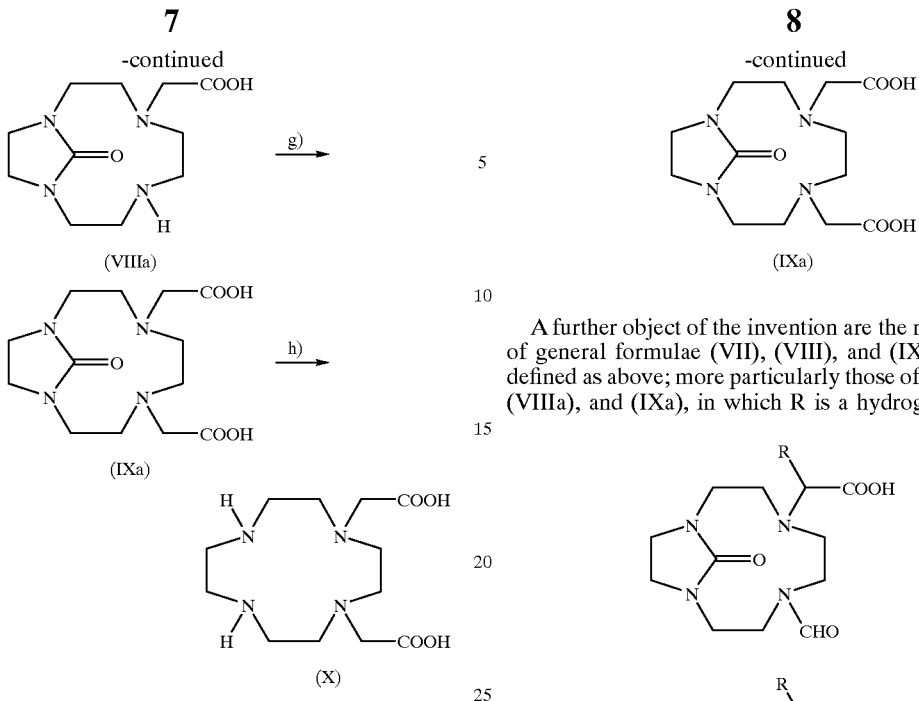

A further object of the invention are the novel compounds of general formulae (VII), (VIII), and (IX), in which R is defined as above; more particularly those of formulae (VIIa), (VIIIa), and (IXa), in which R is a hydrogen atom in which in step e) and g) the alkylating agent is the compound of formula XCH$_2$COOH and through formation of the novel intermediate compounds:

7-formyl-1,4,7,10-tetraazabicyclo[8.2.1]tridecane-13-on-4-acetic acid of formula (VIIa); 1,4,7,10-tetraazabicyclo[8.2.1]tridecane-13-on-4-acetic acid of formula (VIIIa); 1,4,7,10-tetraazabicyclo[8.2.1]tridecane-13-on-4,7-diacetic acid of formula (IXa).

The preferred conditions in the presence of BrCH$_2$COOH as alkylating agent, are at least 1.5 mols of alkylating agent per mol of starting product and the temperature is 45° C.; the reaction time is 21 hours; and pH is 11.5.

Steps e) and 9) are carried out using the same alkylating agent, namely BrCH$_2$COOH, and the same conditions can therefore be used for the two steps.

It is moreover possible to directly alkylate compound (V) or compound (VI) with at least 4 mols of XCH$_2$COOH, preferably BrCH$_2$COOH, per mol of starting product, at a temperature of 90° C. and at basic pH, thus obtaining compound (IXa), without the step of formation of the intermediates shown above, as represented in the following Scheme:

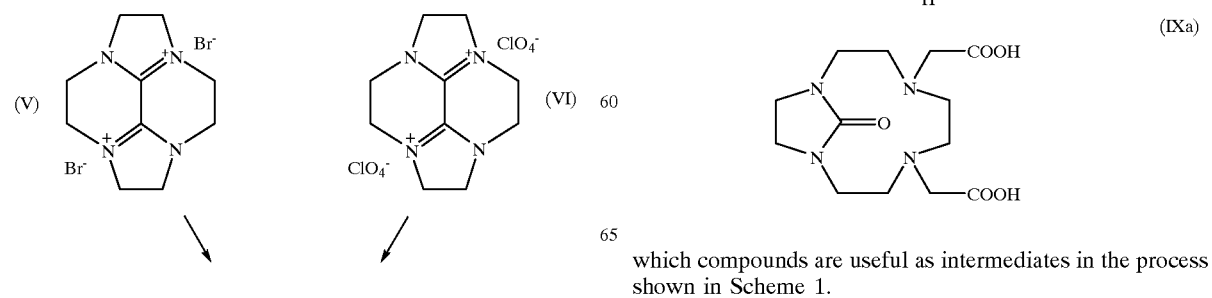

which compounds are useful as intermediates in the process shown in Scheme 1.

Analogously to 1,4,7,10-tetraazacyclododecane-1,4-diacetic acid, the novel chelating agents were prepared: α,α'-dimethyl-1,4,7,10-tetraazacyclododecane-1,4-diacetic acid, in which R in formula (I) is methyl; α,α'-diethyl-1,4,7,10-tetraazacyclododecane-1,4-diacetic acid, in which R is ethyl; α,α'-dibenzyl-1,4,7,10-tetraazacyclododecane-1,4-diacetic acid, in which R is benzyl.

In this case also the process for the preparation of the novel chelated complexes involves novel intermediate compounds, namely: α-methyl-7-formyl-1,4,7,10-tetraazabicyclo[8.2.1]tridecane-13-on-4-acetic, α-methyl-1,4,7,10-tetraazabicyclo[8.2.1]tridecane-13-on-4-acetic, α,α'-dimethyl-1,4,7,10-tetraazabicyclo[8.2.1]-tridecane-13-on-4,7-diacetic acids;

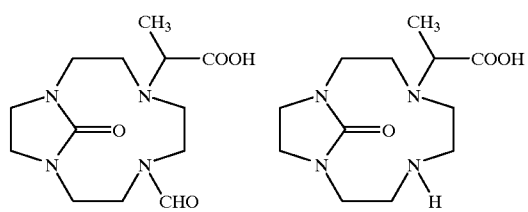

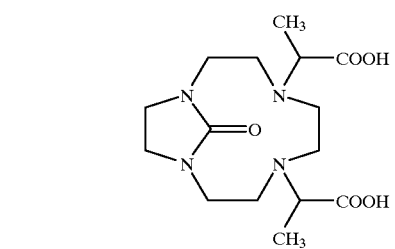

α-ethyl-7-formyl-1,4,7,10-tetraazabicyclo[8.2.1]tridecane-13-on-4-acetic, α-ethyl-1,4,7,10-tetraazabicyclo-[8.2.1]tridecane-13-on-4-acetic, α,α'-diethyl-1,4,7,10-tetraazabicyclo[8.2.1]tridecane-13-on-4,7-diacetic acids;

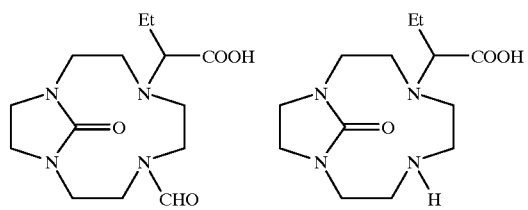

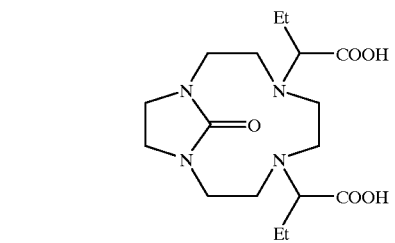

α-benzyl-7-formyl-1,4,7,10-tetraazabicyclo[8.2.1]tridecane-13-on-4-acetic, α-benzyl-1,4,7,10-tetraazabicyclo-[8.2.1]tridecane-13-on-4-acetic, α,α'-dibenzyl-1,4,7,10-tetraazabicyclo[8.2.1]tridecane-13-on-4,7-diacetic acids.

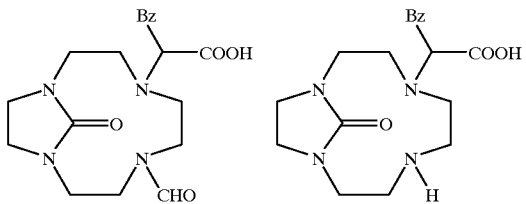

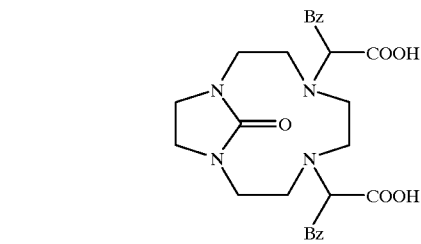

It has also surprisingly been found that the hydrolysis of compounds (VII) and (VIII), and in particular (VIIa) and (VIIIa), in basic conditions (pH>13), obtained by addition of a base, preferably NaOH or KOH, at high temperature (150–220° C., preferably 180–200° C.) and under pressure, yields compounds of formula (XI), in which R is defined as above.

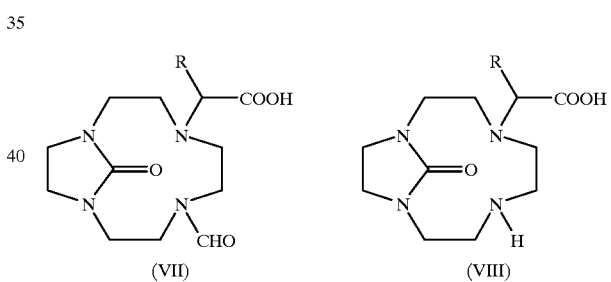

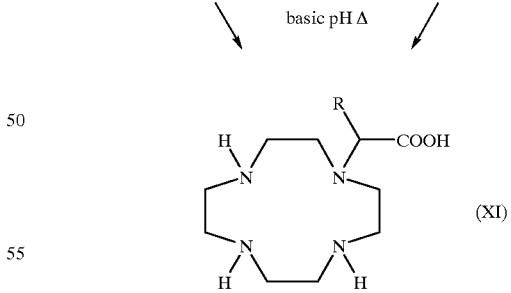

Said compounds are useful both as chelating agents for metal ions, and for the preparation of variously substituted chelating agents.

The process is particularly preferred for the preparation of the already known compound, 1,4,7,10-tetraazacyclododecane-1-acetic acid (see Meunier et al., Can. J. Chem., 73, 685, 1995), when R is a hydrogen atom.

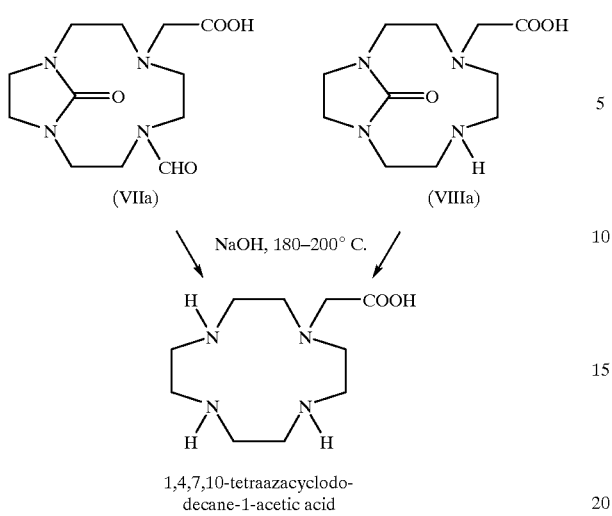

(VIIa)     (VIIIa)

NaOH, 180–200° C.

1,4,7,10-tetraazacyclodo-
decane-1-acetic acid

Also in this case the process for the preparation of this compound is more efficient and more suited for the industrial application than that already described in literature.

It is also an object of the invention the process for the preparation of compounds (I), comprising the steps represented in the following Scheme 3:

Scheme 3

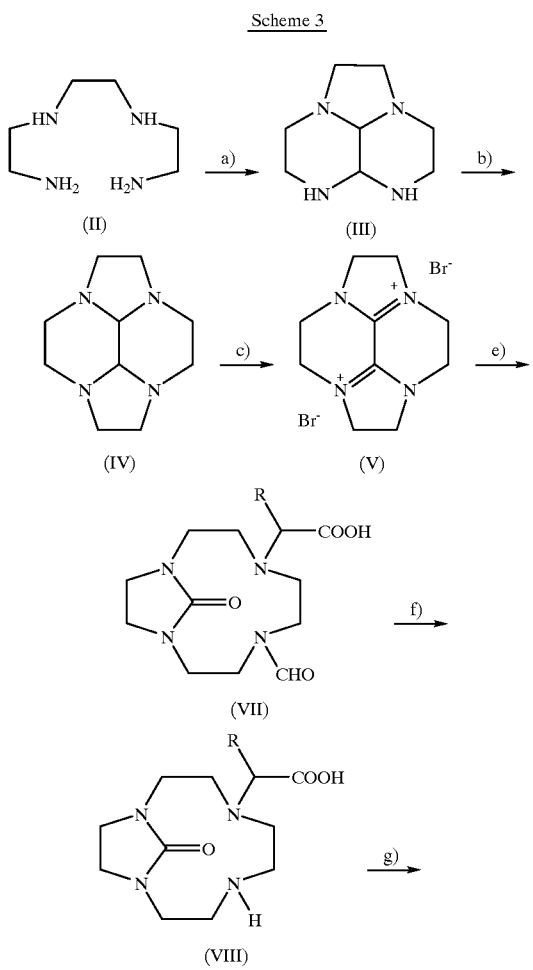

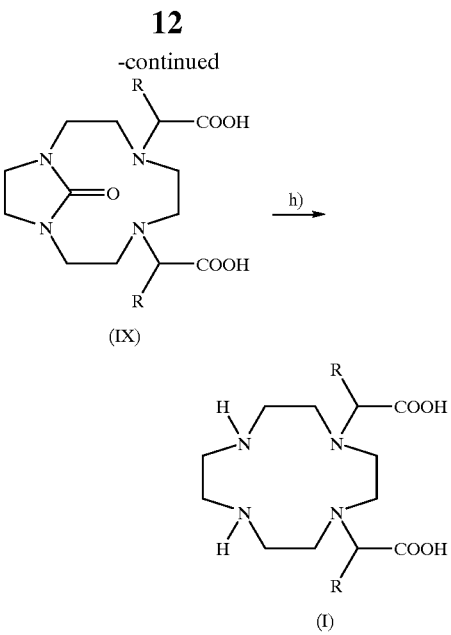

(IX)

(I)

in which step d) of the above Scheme is omitted and compound (V) is directly alkylated according to the procedure described in step e) of Scheme 1, to give compound (VII).

Particularly preferred is the process according to Scheme 3 for the preparation of compound (X), in which R is a hydrogen atom.

The compounds of general formula (I) are in their turn useful substrates for the preparation of compounds of general formula (XII),

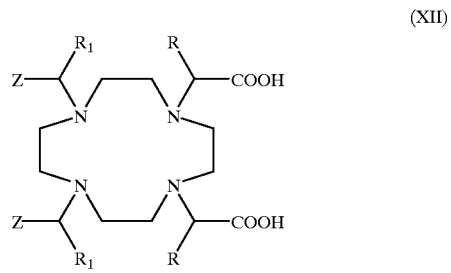

in which

R has the same meanings as defined above;

$R_1$ is a hydrogen atom, a straight or branched or cyclic $C_1$–$C_6$ alkyl group, unsubstituted or substituted by 1 to 10 oxygen atoms, or a $C_1$–$C_{20}$ alkyl group, optionally interrupted by a phenylene, phenyleneoxy or phenylenedioxy in its turn substituted by a straight or branched $C_1$–$C_6$ alkyl group, unsubstituted or substituted by 1 to 7 hydroxy groups or 1 to 3 $C_1$–$C_7$ groups; the aromatic group being unsubstituted or substituted by alkoxy groups or by halogens, carboxy, carbamoyl, alkoxycarbonyl, sulfamoyl, hydroxyalkyl, amino, acylamino, acyl, hydroxyacyl;

Z is one of the following groups

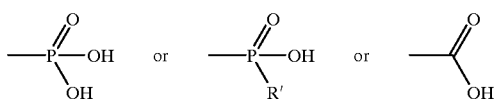

R' independently of $R_1$, has the same meanings as $R_1$ except for the hydrogen atom.

The compounds of formula (XII) are useful as chelating agents of paramagnetic metal ions, for the preparation of contrast agents for NMR diagnostics, as described for example in EP 325762.

Particularly preferred are the compounds of general formula (XIII),

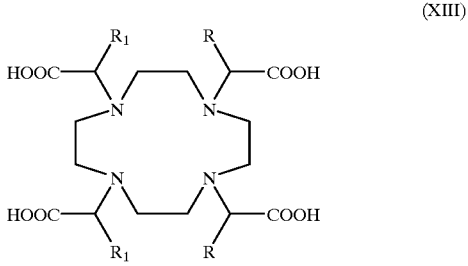

(XIII)

in which R and $R_1$ have the meanings defined above.

It is also an object of the present invention the process for the preparation of compounds (XIII), starting from compounds (I) by alkylation, according to known methods, with an excess of an alkylating agent $R_1$—CH($X_1$)—COY of formula (XIV), represented in the following Scheme 4:

Scheme 4

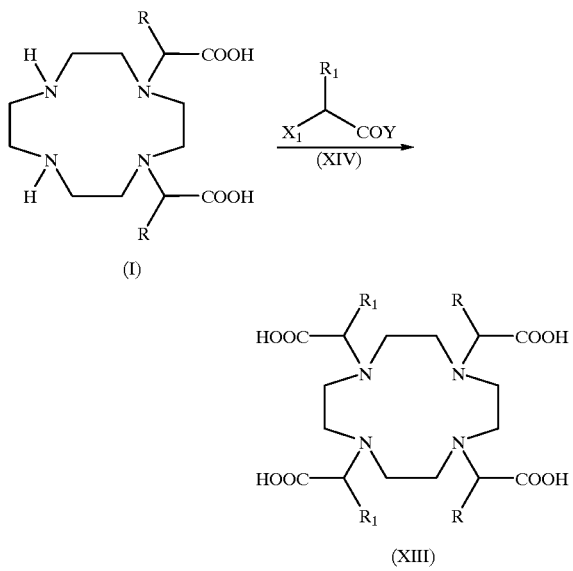

in which
$R_1$ and R have the meanings as defined above;
$X_1$ is a halogen or a sulfonic acid reactive residue;
Y is a —OH or —$OR_2$ group, wherein $R_2$ is a straight or branched $C_1$–$C_4$ alkyl group; when Y is —$OR_2$, the ester groups are hydrolysed to obtain compounds of formula (XIII).

Alkylating agents of formula (XIV) corresponding to compound $R_1$—CH($X_1$)—COOH, in which $X_1$ is bromine or chlorine, are preferred, particularly preferred being the alkylating agents of formula $X_1CH_2COOH$, in which R is the hydrogen atom, and $X_1$ is bromine or chlorine.

In the other cases the alkylating agent of formula (XIV) can be selected from the compounds which are already commercially available or whose preparation has already been described in literature (see for example WO 93/24469 or EP 325762), or those still to synthesize, using for example known methods for the preparation of suitable precursors (for example, for acyl chloride α-halogen derivatives, see: Harpp et al., J. Org. Chem., 40. 3420. 1975), and subsequent transformation into the desired product.

Preferably $R_1$ can be selected from the group consisting of: H or a straight or branched alkyl group, such as a methyl, ethyl, propyl, isopropyl, butyl, isobutyl group, in its turn substituted by hydroxy groups or interrupted by oxygen atoms, as defined above.

When an aromatic group is present in $R_1$, particularly preferred are the phenyl, benzyl, phenylmethoxymethyl groups.

Particularly preferred are 3-(phenylmethoxy)-propanoic acid reactive derivatives, such as 2-bromo-3-(phenylmethoxy)propanoic acid, the preparation of which is described in Grossman et al., Chem. Ber., 91, 538, 1958, and 2-chloro-3-(phenylmethoxy)propanoic acid (CAS RN 124628-32-6), prepared analogously to the brominated derivative.

On the other hand, $R_2$ is preferably selected from the group consisting of: methyl, ethyl, isopropyl, butyl, tert-butyl.

The reactive group $X_1$ can be selected, by way of example, as already mentioned, from the group consisting of halogens (Cl, Br, I), or it can be a mesylate ($MeSO_2O^-$), benzenesulfonyloxy ($PhSO_2O^-$), nitrobenzenesulfonyloxy (p-$NO_2PhSO_2O^-$), tosylate ($TsO^-$), or triflate ($CF_3SO_3^-$) group.

The alkylation of compounds (I), when Y is the hydroxy group, can conveniently be performed as shown in Scheme 1 above.

Particularly preferred are the alkylating agents of general formula (XIV), in which Y is a hydroxy group, corresponding to bromoacetic acid (commercially available product), 2-bromopropionic acid (commercially available product), 2-bromobutyric acid (commercially available product).

The reaction solvent can suitably be selected from dipolar aprotic solvents, in particular from dimethylformamide (DMF), dimethylacetamide (DMA), dimethylsulfoxide (DMSO), acetonitrile ($CH_3CN$) and N-methylpyrrolidone, and the reaction is carried out in the presence of an organic base, preferably a tertiary aliphatic amine selected from triethylamine (TEA), diisopropylethylamine and tributylamine.

In this case it can be convenient to also transform the acid groups present in the compound of formula (I), into the ester group —$OR_2$, in order to promote the alkylation reaction, depending on the reactivity of the alkylating agent itself.

The reaction temperature will range, in this case, from 0 to 80° C., depending on the reactivity of the selected alkylating agent.

In this case, the alkylation reaction will be followed by basic hydrolysis of the resulting diester, in conventional conditions, to obtain the desired compound of general formula (XIII).

By way of example of the huge potentialities provided by this synthetic route, the Experimental section describes the synthesis of the novel compound, α,α'-bis(methyl)-1,4,7,10-tetraazacyclo-dodecane-1,4,7,10-tetraacetic acid:

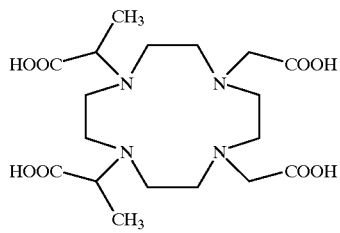

as well as that of α,α'-bis[(phenylmethoxy)methyl]-1,4,7,10-tetraazacyclododecane-1,4,7,10-tetraacetic acid

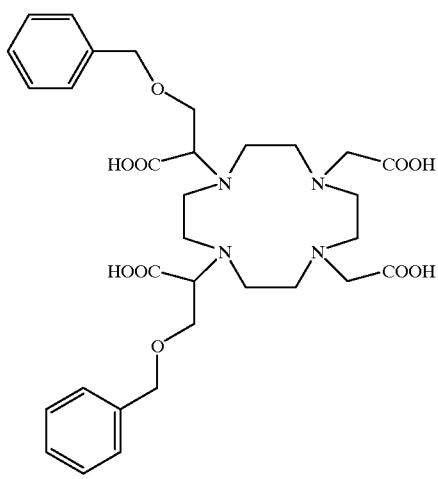

which by catalytic hydrogenation, as described in example 6 of EP 325762, yields α,α'-bis(hydroxymethyl)-1,4,7,10-tetraazacyclododecane-1,4,7,10-tetraacetic acid.

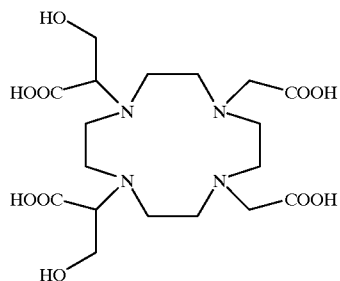

On the other hand, when in compounds (XII) Z is a phosphonic or phosphinic group, said compounds are prepared according to methods known in literature. More specifically, phosphonic derivatives are obtained from hydrochlorides or hydrobromides of the corresponding cyclic amines by reaction with formaldehyde and phosphorous acid ($H_3PO_3$) (see Sherry et al., Inorg. Chem., 28, 3336, 1989). The phosphine compounds are obtained from compound (I), previous esterification (e.g. formation of the t-butyl ester) by reaction with the corresponding phosphine derivative (such as diethoxymethylphosphine, $(EtO)_2PMe$) and paraformal-dehyde, in anhydrous solvents. The resulting diester from the condensation is hydrolysed in acid solution at high temperature, to obtain the corresponding alkylphosphinic acid (see, e.g. Parker et al., J. Chem.Soc. Chem. Commun., 1738, 1990).

The synthesis of the novel compound, 1,4,7,10-tetraazacyclododecane-1,4-diacetic-7,10-dimethylenediphosphonic acid of formula (XV), starting from compound (I), according to methods known in literature, is reported in the Experimental section.

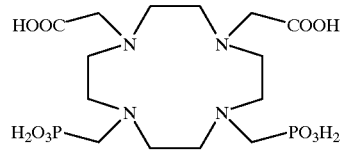

In the following, some preparation examples according to the method of the present invention are reported.

Experimental Section

EXAMPLE 1

2,3,4,6,7,8-Hexahydro-1H,5H-4a,6a-diaza-2a,8a-azoniacyclopent[fg]acenaphthylene diperchlorate

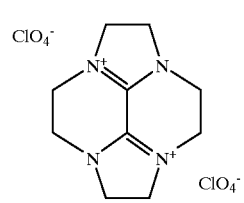

A) Triethylenetetramine hydrate 520 g of commercial triethylenetetramine (starting purity 62%, GC in % area) are dissolved in 800 mL of toluene. 80 mL of water are added under stirring, the mixture is cooled at 25° C. and seeded with purified triethylenetetramine. The suspension is stirred for 45 min. at 20° C., then cooled at 5–10° C. for 1 h. The crystallized solid is filtered, washed with some toluene, then dried at 30° C. under vacuum for 8 h. 365 g of desired product are obtained. Yield: 91% on theoretical Water content: 17% GC: 97% (in % area)

B) 3H,6H-2a,5,6,8a-Octahydro-tetraazacenaphthylene

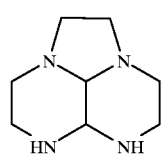

A solution of triethylenetetramine hydrate (100 g, 0.54 mol) in water (1 L) is added with 80 g (1.08 mol) of calcium hydroxide. The milky suspension is cooled to a temperature of 5° C., then added with a 5% glyoxal aqueous solution (626 g, 0.54 mol) under stirring. After 2 h the reaction is completed (absence of triethylenetetramine, GC analysis). After warming at a temperature of 20° C., the insoluble inorganic solid is filtered off and washed with water. The filtrate is concentrated to dryness under vacuum in rotating evaporator.

100 g of the desired intermediate in the form of a colourless oily liquid are obtained. (GC purity: >75%)

Yield: 70%.

$^1$H-NMR, $^{13}$C-NMR, IR and MS spectra are consistent with the indicated structure.

C) 2a,4a,6a,8a-Decahydro-tetraazacyclopent[fg]
acenaphthylene (IV)

266 g (1.58 mol) of 3H,6H-2a,5,6,8a-octahydrotetraazacenaphthylene are added with 4.4 L of dimethylacetamide, 837 g of $Na_2CO_3$ (7.9 mol) and 81.3 g of NaBr (0.79 mol). The suspension is heated to 58° C., then 469 g of 1,2-dichloroethane (4.74 mol) dissolved in 800 mL of DMAC are added under stirring. The mixture is heated to 80° C. and reacted for 3 h. The suspension is cooled, salts are filtered off, the filtrate is added with 192 g of celite and the solvent is distilled off under reduced pressure. The residue is taken up with hexane and 4 solid-liquid extractions are performed. The organic extracts are concentrated to dryness to obtain 184 g of the desired product (0.94 mol).

Yield 59%

GC: 98.5% (in % area)

$^1$H-NMR, $^{13}$C-NMR, IR and MS spectra are consistent with the indicated structure.

D) 2,3,4,6,7,8-Hexahydro-1H,5H-4a,6a-diaza-2a,8a-azoniacyclopent [fg]acenaphthylene diperchlorate 50.4 g (0.259 mol) of 2a,4a,6a,8a-decahydrotetraazacyclopent [fg] acenaphthylene are dissolved in 955 g of demineralized water. 290 g of 1N HCl are added to pH 4.5, then the solution is cooled at 20° C. and 104.93 g (0.65 mol) of bromine and, at the same time, 1.256 kg of 1N NaOH, are dropped therein to keep pH at 4.5. The mixture is reacted overnight at room temperature, the solution is concentrated under reduced pressure and at 50° C. to a weight of 0.73 kg, then cooled to 25° C. and added with 146 g of a 50% w/w aqueous solution of sodium perchlorate monohydrate, under stirring. After 2 h the precipitate is filtered and washed with water. After drying in static drier under vacuum at 50° C., 61.34 g (0.156 mol) of product are obtained. Yield: 60%.

Electrophoretic Method

| Capillary: | fused silica 0.56 m × 75 mm |
|---|---|
| Voltage: | 12 kV |
| Buffer | 0.05M phosphate pH 4.5 |
| Temperature: | 40° C. |
| Stoptime: | 20 min. |
| Detection: (UV) | 200–220 nm |
| Injection: | hydrostatic (50 mbar, 3s) |
| Sample conc.: | 1 mg/mL |
| Instrumentation: | Hewlett Packard 3D HPCE |

Preconditioning timetable:

| t (min) | action |
|---|---|
| 0 | washing with $H_2O$ |
| 2 | washing with 0.1M NaOH |
| 4 | washing with $H_2O$ |
| 5 | washing with buffer |
| 9 | start analysis |

EXAMPLE 2

Synthesis of 7-formyl-1,4,7,10-tetraazabicyclo
[8.2.1]tridecane-13-on-4-acetic acid (VIIa)

20 g (0.051 mol) of compound (VI) prepared in Example 1 are suspended in 200 mL of demineralized water. 2N NaOH is added to reach pH 12 and the mixture is heated at 45° C. A 80% w/w bromoacetic acid aqueous solution (19.5 g, 0.11 mol) and 2N NaOH are dropped simultaneously to keep pH 12. The mixture is reacted for 5 h at 45° C. The solution is cooled and acidified to pH 1.1 with 34% w/w HCl. The suspension is stirred for 3 hours at 22° C. and filtered by suction, washing the solid on the filter with demineralized water. After drying in static drier under vacuum, 18.67 g (0.048 mol) of the desired product are obtained, which is isolated as perchlorate.

Yield: 94%

$^1$H-NMR, $^{13}$C-NMR, IR and MS spectra are consistent with the indicated structure.

Analogously are prepared:

α-methyl-7-formyl-1,4,7,10-tetraazabicyclo[8.2.1]
tridecane-13-on-4-acetic acid;

α-ethyl-7-formyl-1,4,7,10-tetraazabicyclo[8.2.1]tridecane-13-on-4-acetic acid;

α-benzyl-7-formyl-1,4,7,10-tetraazabicyclo[8.2.1]
tridecane-4-acetic acid.

EXAMPLE 3

Synthesis of 1,4,7,10-tetraazabicyclo[8.2.1]
tridecane-13-on-4-acetic acid (VIIIa)

10 g (0.026 mol) of compound (VIIa) prepared in Example 2, are suspended in 100 mL of demineralized water. 2N NaOH is added to pH 12 and the mixture is heated at 90° C. for 5 hours keeping the desired pH by addition of 2N NaOH. The solution is cooled at 22° C. and adjusted to pH 1.1 by acidification with 34% HCl (w/w). The solution is partially concentrated in rotating evaporator and the inorganic precipitate is filtered. The solution is percolated on 0.38 L of polystyrene adsorbing resin XAD-1600 eluting with demineralized water. The fractions containing the product free from chloride ions are collected, combined and concentrated to a residue in rotating evaporator.

5.35 g (0.015 mol) of the desired product are obtained as the perchlorate.

Yield: 57%

$^1$H-NMR, $^{13}$C-NMR, IR and MS spectra are consistent with the indicated structure.

Analogously are prepared:
α-methyl-1,4,7,10-tetraazabicyclo[8.2.1]tridecane-13-on-4-acetic acid;
α-ethyl-1,4,7,10-tetraazabicyclo[8.2.1]tridecane-13-on-4-acetic acid;
α-benzyl-1,4,7,10-tetraazabicyclo[8.2.1]tridecane-13-on-4-acetic acid.

EXAMPLE 4

Synthesis of 1,4,7,10-tetraazabicyclo[8.2.1]tridecane-13-on-4,7-diacetic acid

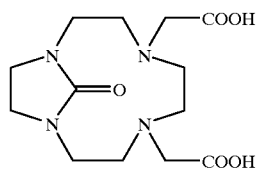

(IXa)

20 g (0.051 mol) of compound (VI) prepared in Example 1 are suspended in 200 ml of demineralized water. 35% NaOH (w/w) is added to pH 11.5, while dropping 22.06 g (0.127 mol) of a 80% (w/w) bromoacetic acid aqueous solution and 2N NaOH to keep pH 11.5 during the addition, in four hours, heating to a temperature of 90° C. At the end of the addition the reaction is completed keeping the solution at 45° C. for a further 3 hours. The solution is acidified with a 34% HCl solution (w/w) to pH 1.1 and percolated on a column containing 2.2 L of adsorbing resin XAD-1600. The fractions containing the product purified and free from inorganic salts are collected and concentrated to a solid residue.

13.2 g (0.042 mol) of the desired product are obtained.

Yield: 82%

$^1$H-NMR, $^{13}$C-NMR, IR and MS spectra are consistent with the indicated structure.

Analogously are prepared:
α,α'-dimethyl-1,4,7,10-tetraazabicyclo[8.2.1]tridecane-13-on-4,7-diacetic acid;
α,α'-diethyl-1,4,7,10-tetraazabicyclo[8.2.1]tridecane-13-on-4,7-diacetic acid;
α,α'-dibenzyl-1,4,7,10-tetraazabicyclo[8.2.1]tridecane-13-on-4,7-diacetic acid.

EXAMPLE 5

Alternative to Example 4 Without Recovery of Compound (VI)

29.1 g (0.15 mol) of compound (IV) prepared in Example 1 are dissolved in 570 g of demineralized water. 174 g of 1N HCl are added reach to pH 4.5, then the solution is cooled at 20° C. and 60 g (0.375 mol) of bromine and 0.75 kg of 1N NaOH are dropped therein simultaneously, to keep pH at 4.5. After reacting overnight at room temperature, the solution is concentrated to 200 g under reduced pressure and at 50° C. The resulting solution is added dropwise with 104.3 g (0.6 mol) of 80% w/w bromoacetic acid solution at 90° C. during 5 hours, keeping pH 11.5. The resulting solution is kept at this pH and at this temperature for 5 hours, to obtain a solution that is cooled to 23° C. and acidified to pH 1.1 with a 34% w/w HCl solution. After partial concentration to 530 g, the solution is percolated on a column containing 4.2 L of polystyrene adsorbing resin XAD-1600, eluting with demineralized water and collecting the fractions containing the product useful and free from salts, which are combined and concentrated to a solid residue.

33 g (0.105 mol) of 1,4,7,10-tetraazabicyclo[8.2.1]tridecane-13-on-4,7-diacetic acid are obtained.

Yield: 70

EXAMPLE 6

Synthesis of 1,4,7,10-tetraazacyclododecane-1,4-diacetic acid

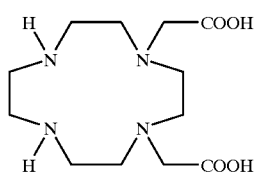

(X)

11.63 g (0.037 mol) of compound (IXa) prepared in Example 4 are suspended in a solution containing 50 mL of demineralized water and 24.9 g of 30% w/w NaOH. The resulting solution is placed in autoclave Parr and heated at 195° C. for 22 hours, then acidified to pH 4 by adding dropwise 20 g of a solution of 34% w/w HCl and filtered through paper. The resulting solution is purified on a strongly anionic ion-exchange resin and on polyvinylpyridine resin and the product is recovered by crystallization from a methanol/acetone solution.

6.34 g (0.022 mol) of the desired product are obtained.

Yield: 60%

$^1$H-NMR, $^{13}$C-NMR, IR and MS spectra are consistent with the indicated structure.

Analogously are prepared:
α,α'-dimethyl-1,4,7,10-tetraazacyclododecane-1,4-diacetic acid;
α,α'-diethyl-1,4,7,10-tetraazacyclododecane-1,4-diacetic acid;
α,α'-dibenzyl-1,4,7,10-tetraazacyclododecane-1,4-diacetic acid.

EXAMPLE 7

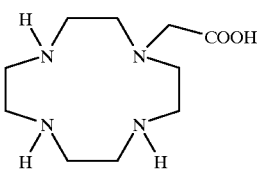

15 g (0.038 mol) of compound (VIIa) prepared in Example 2 are suspended in 50 mL of demineralized water and 25.3 g of 30% w/w NaOH. The suspension is placed in autoclave Parr and heated at 195° C. for 16 hours. The resulting solution is purified on a strongly anionic ion-exchange resin, on a polyvinylpyridine resin and on adsorbing resin XAD-1600. The obtained fractions, containing the purified product, are combined and concentrated to a solid residue.

5.1 g (0.022 mol) of the desired product are thereby obtained.

Yield: 58%

$^1$H-NMR, $^{13}$C-NMR, IR and MS spectra are consistent with the indicated structure.

EXAMPLE 8

Synthesis of 1,4,7,10-tetraazacyclododecane-1,4-diacetic acid-7,10-dimethylenediphosphonic acid

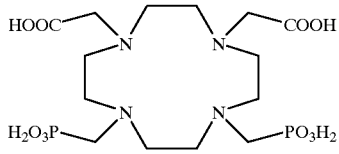

(XV)

5.8 g (0.02 mol) of compound (X) obtained in Example 6 are added to 60 mL of 15% w/w HCl and $H_3PO_3$ (4.1 g, 0.05 mol). The solution is heated to reflux, then 5.94 ml of a 37% w/w formaldehyde solution (0.08 mol) are dropped therein in 30 minutes. The solution is refluxed for 5 hours, then concentrated to an oily residue. The product is purified by crystallization from water, then dried thereby obtaining 4.8 g (0.01 mol) of the desired product.

Yield: 50%

$^1$H-NMR, $^{13}$C-NMR, IR and MS spectra are consistent with the indicated structure

EXAMPLE 9

Synthesis of α,α'-bis(methyl)-1,4,7,10-tetraazacyclododecane-1,4,7,10-tetraacetic acid

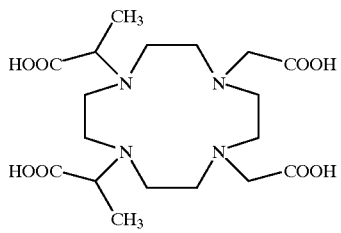

5 g (0.017 mol) of 1,4,7,10-tetraazacyclododecane-1,4-diacetic acid, prepared according to Example 6, are diluted with 45 g of water and slowly added with a solution prepared dissolving 8.04 g (0.051 mol) of 2-bromopropionic acid in 40 mL of water. The mixture is reacted at 45° C. for 12 h, keeping pH at 10.5–11 by addition of 2N NaOH, cooled at room temperature and acidified to pH 2 with conc. with hydrochloric acid. After 1 h the precipitated solid is filtered, and the filter is washed with demineralized water. The crude product is redissolved in 600 mL of polyvinylpyridine resin (PVP), eluting repeatedly with water. The useful fractions are combined, concentrated to dryness under vacuum and dried in static drier at 50° C. under vacuum, thereby obtaining 5.7 g (0.013 mol) of the desired product.

Yield: 76%

$^1$H-NMR, $^{13}$C-NMR, IR and MS spectra are consistent with the indicated structure.

EXAMPLE 10

Synthesis of α4, α7-bis[(phenylmethoxy)methyl]-1,4,7,10-tetraazacyclododecane-1,4,7,10-tetraacetic acid

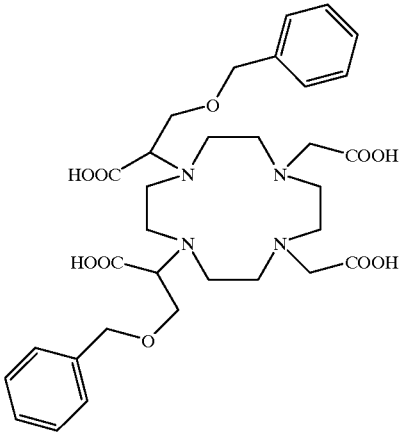

1,4,7,10-Tetraazacyclododecane-1,4-diacetic acid is reacted with 2-bromo-3-(phenylmethoxy)propanoic acid methyl ester or with 2-trifluoromethanesulfonate-2-(phenylmethoxy)-propanoic acid methyl ester in DMF and in the presence of triethylamine. The methyl ester is hydrolysed to obtain the desired product.

$^1$H-NMR, $^{13}$C-NMR, IR and MS spectra are consistent with the indicated structure.

EXAMPLE 11

Synthesis of α1,α4-bis(hydroxymethyl)-1,4,7,10-tetraazacyclododecane-1,4,7,10-tetraacetic acid

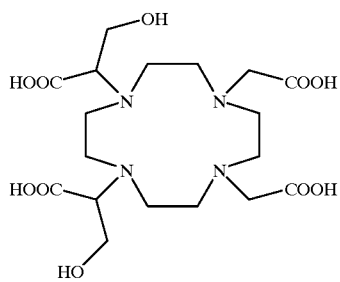

The product obtained in Example 10 is subjected to catalytic hydrogenation in the presence of 5% Pd/C, to obtain, after adsorption of the necessary hydrogen, the desired product.

$^1$H-NMR, $^{13}$C-NMR, IR and MS spectra are consistent with the indicated structure.

EXAMPLE 12

Preparation of 1,4,7,10-tetraazacyclododecane-1,4-diacetic acid manganese complex

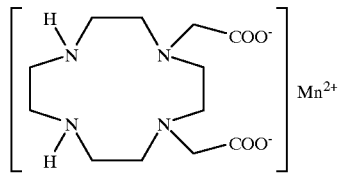

8.66 g of compound (X) prepared as described in Example 6 (30 mmol) are dissolved in 30 mL of water. pH is adjusted to 6.8 by addition of a solution of 1-deoxy-1-(methylamino)-D-glucitol (0.3 mL; 0.3 mmol); after that MnCl$_2$ (30 mL; 30 mmol) is added during two hours, maintaining pH 6.8 by addition of 1-deoxy-1-(methylamino)-D-glucitol (28.2 mL; 28.2 mL). After 24 h the solution is filtered through a Millipore® filter (HA-0.22 mm), nanofiltered, evaporated and the residue is dried on P$_2$O$_5$ to give the desired product (5.0 g; 14.65 mmol). The permeate containing the desired product is concentrated to 50 mL and the resulting solid (meglumine chloride) is filtered and removed. The solution is evaporated to a residue, that is crystallized from MeOH (50 mL) to yield 3 g of a second crop of the desired product (8.0 mmol).

Yield: 76%

$^1$H-NMR, $^{13}$C-NMR, IR and MS spectra are consistent with the indicated structure.

What is claimed is:
1. A process for the preparation of a compound of formula (I) starting from triethylenetetramine of formula (II), as represented in Scheme 1:

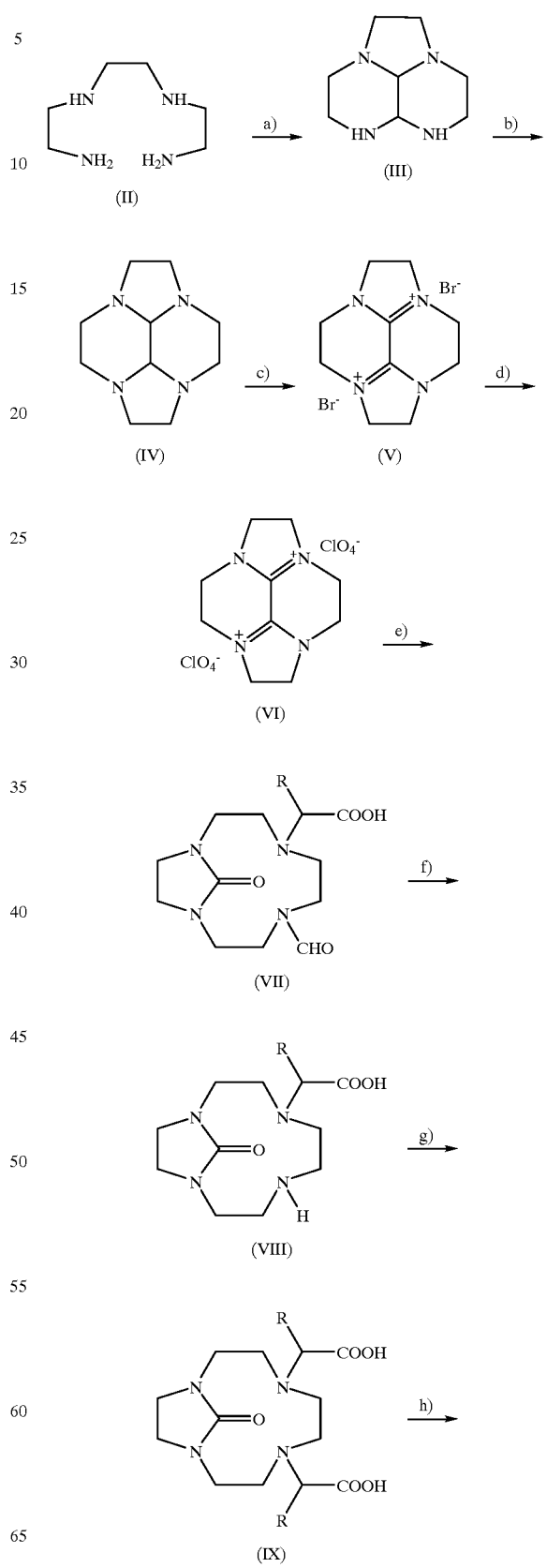

Scheme 1

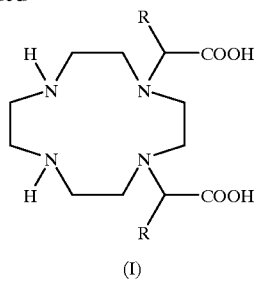

(I)

said process comprising the steps of:
(a) condensing a triethylenetetramine of formula (II) with a glyoxal derivative, in water or in a water-soluble solvent or a mixture thereof, at a temperature of 0–50° C., in the presence of a stoichiometric amount or a slight excess of calcium hydroxide to give octahydro-3H,6H-2a,5,6,8a-tetraazacenaphthylene of formula (III);
(b) condensing the compound from step a) with an alkylating agent —$CH_2$—$CH_2$—X, in which X is Cl or Br, in amounts from 1 to 5 mols per mol of compound (III), in a dipolar aprotic solvent and in the presence of an alkali or alkaline-earth metal carbonate base, in amounts from 5 to 10 mols per mol of compound (III), and with the addition of NaY, in which Y is I or Br, as catalyst in amounts from 0.1 to 2 mols per mol of compound (III), wherein X and Y are not at the same time Br, at a temperature from 25 to 150° C., to give decahydro-2a,4a,6a,8a-tetraazacyclopent[fg]acenaphthylene of formula (IV);
(c) oxidizing compound (IV) with bromine at pH 4–5 to give 2,3,4,6,7,8-hexahydro-1H,5H-4a,6a-diaza-2a,8a-azoniacyclopent[fg] acenaphthylene dibromide of formula (V);
(d) forming 2,3,4,6,7,8-hexahydro-1H,5H-4a,6a-diaza-2a,8a-azoniacyclopent[fg]acenaphthylene diperchlorate of formula (VI) by adding perchlorate ions to the solution of compound (V);
(e) alkylating compound (VI) with an alkylating agent of formula R—CH(X)COOH, in which X is a halogen, and R is defined above, under basic conditions, to give a compound of formula (VII);
(f) hydrolyzing the formyl group of compound (VII) under basic conditions to give a compound of formula (VIII);
(g) alkylating compound (VIII) with the alkylating agent of formula R—CH(X)—COOH, in which X and R have the meanings defined above, under basic conditions, to give a compound of formula (IX); and finally
(h) hydrolyzing compound (IX), under basic conditions, to give a compound of formula (I).
2. The process as claimed in claim 1, in which in step (b) the alkylating agent is added in amounts from 1 to 5 mols per mol of compound (II), at temperatures from 30 to 80° C.;
in step (c) oxidation is carried out by adding bromine in amounts of 2–2.5 mols per mol of compound (IV), in aqueous solution at pH 4–5, at temperatures from 17 to 30° C.; in step (d) sodium perchlorate or perchloric acid are added in amounts of 2.5–3 mols per mol of compound (IV);
in step (e) the reaction temperature ranges from 30 to 70° C., pH ranges from 10 to 12 obtained by addition of a base; and the amount of alkylating agent is stoichiometric or in excess;
in step (f) the hydrolysis of compound (VII) is in an aqueous solution at basic pH, and at temperatures from 50 to 100° C.;
step (g) is conducted as described for step (e); and
in step (h) the hydrolysis of a compound of formula (IX) is conducted in aqueous solution at basic pH, obtained by the addition of 3–7 mols of a base, at temperatures of 150–220° C.
3. The process according to claim 1 or 2, in which, in the alkylating agent of formula R—CH(X)—COOH, X is bromine or chlorine.
4. The process as claimed in claim 1, in which in steps (e) and (g) the alkylating agent of formula R—CH(X)—COOH is the compound of formula $XCH_2COOH$ and X is chlorine or bromine and 1,4,7,10-tetraazacyclododecane-1,4-diacetic acid (X) is prepared.
5. The process as claimed in claim 4, in which the alkylating agent in steps (e) and (g) is $BrCH_2COOH$, is added in amounts of at least 1.5 mols of alkylating agent per mol of starting product, at a temperatures of 45° C. and at pH 11.5.
6. The process as claimed in claim 1, in which steps (e), (f) and (g) are replaced by a single step in which compound (V), or compound (VI), is reacted with at least 4 mols of $BrCH_2COOH$, at a temperature of 90° C. and at basic pH and 1,4,7,10-tetraazacyclododecane-1,4-diacetic acid (X) is prepared.
7. Compound of formula (VII):

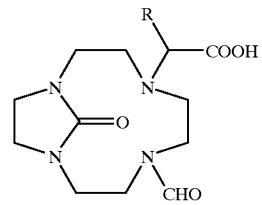

(VII)

in which R is a hydrogen atom, a straight or branched or cyclic $C_1$–$C_6$ alkyl group, the alkyl group unsubstituted or substituted by oxygen atoms, or a $C_1$–$C_{20}$ alkyl group, optionally interrupted by a phenylene, in turn substituted by a straight or branched $C_1$–$C_6$ alkyl group, unsubstituted or substituted by 1 to 3 $C_1$–$C_7$ alkyl groups; wherein the phenylene group is unsubstituted or substituted by alkoxy, carboxy, sulfamoyl, hydroxyalkyl, amino groups; and its complexes with a bivalent or trivalent metal ion having an atomic number from 20 to 31, 39, 42, 43, 44, 49, or from 57 to 83, and its salts with anions of physiologically acceptable organic acids.
8. 7-Formyl-1,4,7,10-tetraazabicyclo[8.2.1]tridecane-13-on-4-acetic acid of formula (VIIa), as claimed in claim 7,

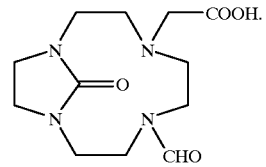

(VIIa)

9. A compound as claimed in claim 7, selected from the group consisting of:

α-methyl-7-formyl-1,4,7,10-tetraazabicyclo[8.2.1]tridecane-13-on-4-acetic acid in which R is a methyl group;
α-ethyl-7-formyl-1,4,7,10-tetraazabicyclo[8.2.1] tridecane-13-on-4-acetic acid in which R is an ethyl group; and
α-benzyl-7-formyl-1,4,7,10-tetraazabicyclo[8.2.1]tridecane-13-on-4-acetic acid in which R is a benzyl group.

10. A compound of general formula (VIII):

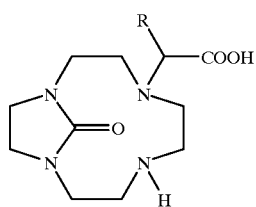

(VIII)

in which R is a hydrogen atom, a straight or branched or cyclic $C_1$–$C_6$ alkyl group, the alkyl group unsubstituted or substituted by oxygen atoms, or a $C_1$–$C_{20}$ alkyl group, optionally interrupted by a phenylene, in turn substituted by a straight or branched $C_1$–$C_6$ alkyl group, unsubstituted or substituted by 1 to 3 $C_1$–$C_7$ alkyl groups; wherein the phenylene group is unsubstituted or substituted by alkoxy, carboxy, sulfamoyl, hydroxyalkyl, amino groups; and its complexes with a bivalent or trivalent metal ion having an atomic number from 20 to 31, 39, 42, 43, 44, 49, or from 57 to 83, and its salts with anions of physiologically acceptable organic acids.

11. 1,4,7,10-Tetraazabicyclo[8.2.1]tridecane-13-on-4-acetic acid of formula (VIIIa).

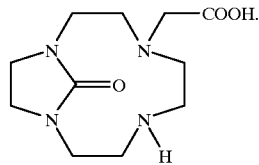

(VIIIa)

12. A compound as claimed in claim 10, selected from the group consisting of:
α-methyl-1,4,7,10-tetraazabicyclo[8.2.1]tridecane-13-on-4-acetic acid, in which R is a methyl group;
α-ethyl-1,4,7,10-tetraazabicyclo[8.2.1]tridecane-13-on-4-acetic acid, in which R is an ethyl group; and
α-benzyl-1,4,7,10-tetraazabicyclo[8.2.1]tridecane-13-on-4-acetic acid, in which R is a benzyl group.

13. A compound of formula (IX),

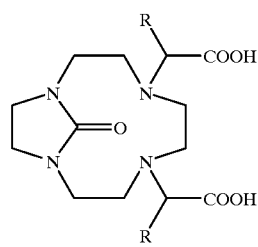

(IX)

in which R is a hydrogen atom, a straight or branched or cyclic $C_1$–$C_6$ alkyl group, the alkyl group is unsubstituted or substituted by oxygen atoms, or a $C_1$–$C_{20}$ alkyl group, optionally interrupted by a phenylene, in turn substituted by a straight or branched $C_1$–$C_6$ alkyl group, unsubstituted or substituted by 1 to 3 $C_1$–$C_7$ alkyl groups; wherein the phenylene group is unsubstituted or substituted by alkoxy, carboxy, sulfamoyl, hydroxyalkyl, amino groups; and its complexes with a bivalent or trivalent metal ion having an atomic number from 20 to 31, 39, 42, 43, 44, 49, or from 57 to 83, and its salts with anions of physiologically acceptable organic acids.

14. 1,4,7,10-Tetraazabicyclo[8.2.1]tridecane-13-on-4,7-diacetic acid of formula (IXa),

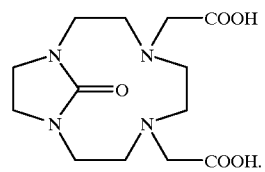

(IXa)

15. A compound as claimed in claim 13, selected from the group consisting of:
αα'-dimethyl-1,4,7,10-tetraazabicyclo[8.2.1]tridecane-13-on-4,7-diacetic acid, in which R is a methyl group;
αα'-diethyl-1,4,7,10-tetraazabicyclo[8.2.1]tridecane-13-on-4,7-diacetic acid, in which R is an ethyl group; and
αα'-dibenzyl-1,4,7,10-tetraazabicyclo[8.2.1]tridecane-13-on-4,7-diacetic acid, in which R is a benzyl group.

16. A process for the preparation of a compound of formula (XI) starting from a compound of formulae (VII) and (VIII), by hydrolysis in basic conditions at high temperature and under pressure:

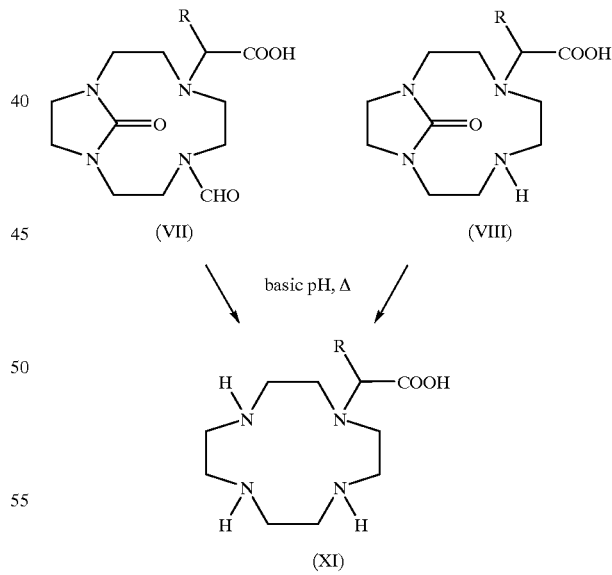

in which R is a hydrogen atom, a straight or branched or cyclic $C_1$–$C_6$ alkyl group, unsubstituted or substituted by 1 to 10 oxygen atoms, or a $C_1$–$C_{20}$ alkyl group, optionally interrupted by a phenylene, in its turn substituted by a straight or branched $C_1$–$C_6$ alkyl group, unsubstituted or substituted by 1 to 3 $C_1$–$C_7$ groups; wherein the phenylene group is unsubstituted or substituted by alkoxy, carboxy, sulfamoyl, hydroxyalkyl, amino groups; and their complexes with bi-trivalent metal ions having atomic number variable from 20 to 31, 39, 42, 43, 44, 49, or from 57 to 83, and their salts with anions of physiologically acceptable organic acids.

17. A process for the preparation of 1,4,7,10-tetraazacyclododecane-1-acetic acid, as claimed in claim 16, starting from compound (VIIa) or (VIIIa), by basic hydrolysis under pressure at a temperature of 180 to 200° C.

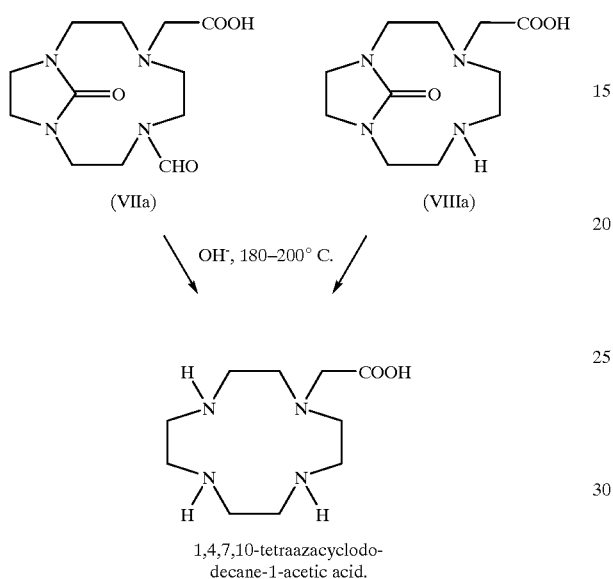

18. A process for the preparation of a compound of formula (I), as represented in the following Scheme 3:

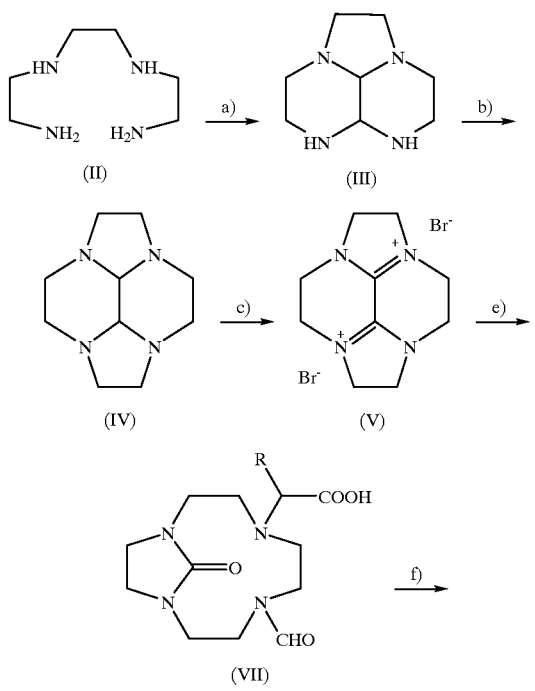

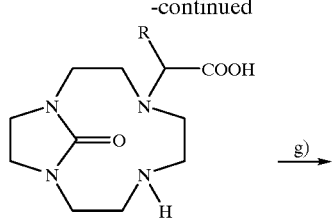

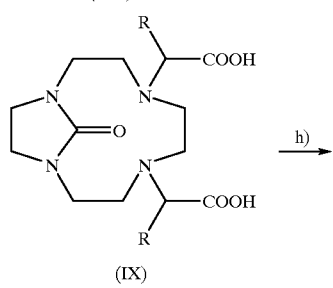

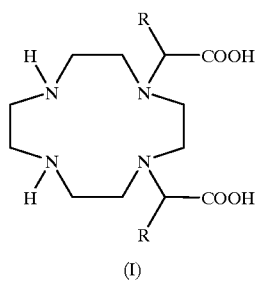

said process comprising the steps of:

(a) condensing a triethylenetetramine of formula (II) with a glyoxal derivative, in water or in a water-soluble solvent or a mixture thereof, at a temperature of 0–50° C., in the presence of a stoichiometric amount or a slight excess of calcium hydroxide to give octahydro-3H,6H-2a,5,6,8a-tetraazacenaphthylene of formula (III);

(b) condensing the compound from step a) with an alkylating agent X—CH$_2$—CH$_2$—X, in which X is Cl or Br, in amounts from 1 to 5 mols per mol of compound (III), in a dipolar aprotic solvent and in the presence of an alkali or alkaline-earth metal carbonate base, in amounts from 5 to 10 mols per mol of compound (III), and with the addition of NaY, in which Y is I or Br, as catalyst in amounts from 0.1 to 2 mols per mol of compound (III), wherein X and Y are not at the same time Br, at a temperature from 25 to 150° C., to give decahydro-2a,4a,6a,8a-tetraazacyclopent[fg]ace-naphthylene of formula (IV);

(c) oxidizing compound (IV) with bromine at pH 4–5 to give 2,3,4,6,7,8-hexahydro-1H,5H-4a,6a-diaza-2a,8a-azoniacyclopent[fg]acenaphthylene dibromide of formula (V);

(d) alkylating compound (VI) with an alkylating agent of formula R—CH(X)COOH, in which X is a halogen, and R is defined above, under basic conditions, to give a compound of formula (VII);

(e) hydrolyzing the formyl group of compound (VII) in basic conditions to give a novel compound of formula (VIII);

(f) alkylating compound (VIII) with the alkylating agent of formula R—CH(X)—COOH, in which X and R have the meanings defined above, under basic conditions, to give a compound of formula (IX); and finally (g) hydrolyzing compound (IX), under basic conditions, to give a compound of formula (I), in which compound (V) is directly alkylated according to the procedure described in step of the same claim, to give compound (VII).

19. The process as claimed in claim 18, for the preparation of 1,4,7,10-tetraazacyclododecane-1,4-diacetic acid, in which R is a hydrogen atom.

20. A process for preparation of a compound (XIII) starting from a compound (I) by alkylation with an excess of an alkylating agent $R_1$—CH($X_1$)—COY of formula (XIV), represented in the following Scheme 4:

Scheme 4

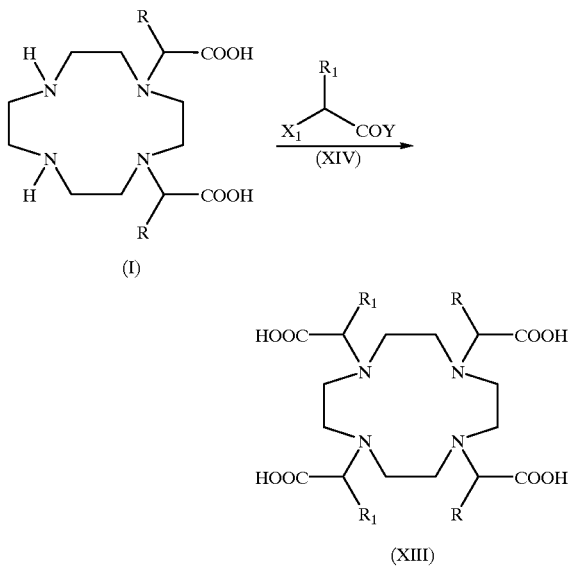

in which
R is a hydrogen atom, a straight or branched or cyclic $C_1$–$C_6$ alkyl group, the alkyl group unsubstituted or substituted by oxygen atoms, or a $C_1$–$C_{20}$ alkyl group, optionally interrupted by a phenylene, in turn substituted by a straight or branched $C_1$–$C_6$ alkyl group, unsubstituted or substituted by 1 to 3 $C_1$–$C_7$ alkyl groups; wherein the phenylene group is unsubstituted or substituted by alkoxy, carboxy, sulfamoyl, hydroxyalkyl, amino groups; and its complexes with a bi- or trivalent metal ion having an atomic number from 20 to 31, 39, 42, 43, 44, 49, or from 57 to 83, and its salts with anions of physiologically acceptable organic acids;

$R_1$ is a hydrogen atom, a straight or branched or cyclic $C_1$–$C_6$ alkyl group, unsubstituted or substituted by 1 to 10 oxygen atoms, or a $C_1$–$C_{20}$ alkyl group, optionally interrupted by a phenylene, phenyleneoxy or phenylenedioxy in turn substituted by a straight or branched $C_1$–$C_6$ alkyl group, unsubstituted or substituted by 1 to 7 hydroxy groups or 1 to 3 $C_1$–$C_7$ groups; wherein the phenylene group is unsubstituted or substituted by an alkoxy group or by halogens, carboxy, carbamoyl, alkoxycarbonyl, sulfamoyl, hydroxyalkyl, amino, acylamino, acyl, hydroxyacyl;

$X_1$ is a halogen or a sulfonic acid reactive residue; and

Y is a —OH, or —$OR_2$ group, wherein $R_2$ is a straight or branched $C_1$–$C_4$ group alkyl; provided that when Y is —$OR_2$, the ester groups are hydrolysed to obtain compounds of formula (XIII).

21. The process as claimed in claim 20, in which the alkylating agent of formula (XIV) is a compound of formula $R_1$—CH($X_1$)—COOH, in which $X_1$ is bromine or chlorine and $R_1$ is selected from the group consisting of hydrogen or a straight or branched alkyl group, in turn substituted by hydroxy groups or interrupted by oxygen atoms.

22. The process as claimed in claim 21, in which the alkylating agent of formula (XIV) is a compound of formula $X_1CH_2COOH$, in which $R_1$ is hydrogen and $X_1$ is bromine or chlorine.

23. The process as claimed in claim 22, in which the alkylating agent of formula (XIV) is selected from the group consisting of bromoacetic acid, 2-bromopropionic acid, and 2-bromobutyric acid.

24. The process as claimed in claim 20, in which, in the alkylating agent of formula (XIV), $R_1$ is selected from the group consisting of phenyl, benzyl, and phenylmethoxymethyl; $X_1$ is selected from the group consisting of mesylate, benzenesulfonyloxy, nitrobenzenesulfonyloxy, tosylate and triflate; and $R_2$ is selected from the group consisting of methyl, ethyl, isopropyl, butyl, and tert-butyl.

* * * * *